(12) United States Patent
Song

(10) Patent No.: US 9,764,070 B2
(45) Date of Patent: Sep. 19, 2017

(54) MEDICAL ASPIRATOR

(71) Applicant: Moohan Enterprise Co., Ltd., Seoul (KR)

(72) Inventor: Hyo Seop Song, Seoul (KR)

(73) Assignee: Moohan Enterprise Co., Ltd., Seoul (KR)

( * ) Notice: Subject to any disclaimer, the term of this patent is extended or adjusted under 35 U.S.C. 154(b) by 349 days.

(21) Appl. No.: 14/369,722

(22) PCT Filed: Dec. 27, 2012

(86) PCT No.: PCT/KR2012/011516
§ 371 (c)(1),
(2) Date: Jun. 30, 2014

(87) PCT Pub. No.: WO2013/100601
PCT Pub. Date: Jul. 4, 2013

(65) Prior Publication Data
US 2014/0358096 A1  Dec. 4, 2014

(30) Foreign Application Priority Data
Dec. 30, 2011 (KR) .................. 10-2011-0147266

(51) Int. Cl.
*A61M 1/00* (2006.01)
(52) U.S. Cl.
CPC ........ *A61M 1/0049* (2013.01); *A61M 1/0009* (2013.01); *A61M 1/0039* (2013.01); *A61M 1/0005* (2013.01); *A61M 2205/071* (2013.01)
(58) Field of Classification Search
CPC .......... A61M 2205/071; A61M 1/0009; A61M 1/0005; A61M 39/10; A61M 2039/1033
See application file for complete search history.

(56) References Cited

U.S. PATENT DOCUMENTS 4,957,487 A * 9/1990 Gerow ............... A61F 5/44
604/133
5,112,323 A * 5/1992 Winkler ............ A61M 1/0011
604/133

FOREIGN PATENT DOCUMENTS

CN    201356886    12/2009
CN    201631745    11/2010
(Continued)

OTHER PUBLICATIONS

International Search Report Dated Apr. 24, 2013 From the Korean Intellectual Property Office Re. Application No. PCT/KR2012/011516 and Its Translation Into English.

*Primary Examiner* — Leslie Deak
*Assistant Examiner* — Kai Weng

(57) ABSTRACT

The present invention is related to a medical aspirator and, in particular, to a medical aspirator comprising: a floor plate; a pressure plate disposed a certain distance away from the floor plate, and defining a discharge hole opened and closed by an opening/closing means; a coil spring installed between the floor plate and the pressure plate; a sealing membrane connecting the edges of the floor plate and the pressure plate, and defining a receiving space capable of receiving bodily fluid between the floor plate and the pressure plate; and a drainage tube connected to the pressure plate, for guiding bodily fluid generated from the body to the receiving space, and including a check valve therein enabling the fluid to flow only in the direction from the body toward the receiving space, wherein the medical aspirator has the effect of preventing contamination from outside air of bodily fluid extracted from the body and stored in the receiving space.

1 Claim, 4 Drawing Sheets

(56) References Cited

FOREIGN PATENT DOCUMENTS

| KR | 0134473 | 10/1998 |
|---|---|---|
| KR | 20-0134473 | 2/1999 |
| KR | 20-0323127 | 8/2003 |
| KR | 20-0339902 | 1/2004 |
| KR | 10-2011-0132712 | 12/2011 |
| WO | WO 2013/100601 | 7/2013 |

* cited by examiner

MEDICAL ASPIRATOR

RELATED APPLICATIONS

This application is a National Phase of PCT Patent Application No. PCT/KR2012/011516 having International filing date of Dec. 27, 2012, which claims the benefit of priority of Korean Patent Application No. 10-2011-0147266 filed on Dec. 30, 2011. The contents of the above applications are all incorporated by reference as if fully set forth herein in their entirety.

TECHNICAL FIELD

This invention is related to a medical aspirator, particularly to a medical aspirator which prevents bodily fluids extracted and stored from the human body from being contaminated by external air. This device allows weak women to use it easily.

BACKGROUND

After surgical operations, blood, exudate and bodily fluids may stay within the organ, and the staying blood or exudate can interferes with wound healing thus it causes a complication. Therefore, doctors use a medical aspirator commonly called "Hemovac" or "Barovac", to prevent the blood or exedate from staying within the organ after the operation.

As shown in FIG. 1, it is common that the existing medical aspirator called Hemovac or Barovac is comprised of a floor plate(10), a pressure plate(20) which is disposed apart from the floor plate(10) by a certain distance, to which a drainage tube(21) is connected, and in which a discharge hole(22) having a stopper(22a) formed therein is formed, a coil spring(30) which is installed between the floor plate(10) and the pressure plate(20), and a sealing membrane(40) which connects the edge of the floor plate(10) and the edge of the pressure plate(20) and forms a space receiving bodily fluids between the floor plate(10) and the pressure plate(20).

However, in order to extract the bodily fluids such as blood, exudates or the like, existing medical aspirators described above require an additional operation to stop the stopper(22a) so as to seal the discharge hole(22) in a state where the pressure plate(20) is pressed down. Therefore, female nurses have difficulties to use this device which needs force.

Also, in a state where the pressure plate(20) rises up to a certain height because nurses cannot overcome the elasticity of the coil spring(30) after pressing the pressure plate(20), when the discharge hole(22) is sealed by the stopper(22a), the bodily fluids are stored in the space within the sealing membrane(40) under where the external air is flowed in the sealing membrane(40). In this case, the bodily fluids may be contaminated by the external air.

DETAILS OF THE INVENTION

Technical Assignment

This invention is designed to overcome the above problems. The air in the empty space formed within the sealing membrane is flowed out through a check valve, so that the gap between the floor plate and the pressure plate is reduced and the external air cannot be flowed into the space within the sealing membrane. As a result, the medical aspirator by the present invention prevents the bodily fluids stored within the sealing membrane from being contaminated by the external air.

Also, after the gap between the floor plate and the pressure plate is reduced, the check valve does not allow the external air to be flowed in, so that the gap between the floor plate and the pressure plate can be maintained. As a result, the medical aspirator by the present invention can be easily used by female nurses with less physical force.

Technical Solution

The medical aspirator according to the present invention includes a floor plate; a pressure plate disposed apart from the floor plate by a certain distance and has an discharge hole being opened and closed by an opening/closing means; a coil spring installed between the floor plate and the pressure plate; a sealing membrane which connects the edge of the floor plate and the edge of the pressure plate and forms a space receiving the bodily fluids between the floor plate and the pressure plate; and a drainage tube which is connected to the pressure plate and guides the bodily fluids to the receiving space and has a check valve formed therein allowing the fluids generated from the human body to flow only in the direction toward the receiving space from the human body. The opening/closing means includes a fixing part which is fixed around the discharge hole of the pressure plate; a first strap which is integrally connected to the fixing part; a fitting tube which is integrally connected to the first strap and is inserted into the discharge hole; a check valve which is inserted within the fitting tube such that the fluids are flowed only in the direction toward the outside from the inside of the receiving space; a second strap which is integrally connected to the fitting tube; and a stopper connected to the second strap seals the top of the fitting tube to where the check valve is inserted.

Here, the drainage tube is comprised of a first connecting tube which is connected to the pressure plate and communicates with the receiving space; a first connector which is fitted to the top of the first connecting tube and has a spiral fitting hole formed downwardly therein passing through the inner and outer surfaces thereof; a second connector which has an insertion protrusion formed on the outer surface thereof in such a manner as to move along the fitting hole of the first connector; and a second connecting tube which is fitted to the top of the second connector.

Advantages of this Invention

In the medical aspirator configured as described above, due to the check valve, the air within the sealing membrane is flowed out and the external air is not flowed into the sealing membrane, thereby preventing bodily fluids stored within the sealing membrane from contamination by the external air.

Also, after the gap between the floor plate and the pressure plate is reduced, the check valve does not allow the external air to be flowed into the internal space of the sealing membrane, so that the reduced gap between the floor plate and the pressure plate is maintained as it is. Therefore, nurses do not have to apply a force to maintain the gap between the floor plate and the pressure plate. Accordingly, an additional operation to insert the stopper into the discharge hole so as to seal the discharge hole is not required.

MODE FOR INVENTION

Hereafter, the embodiment of the medical aspirator according to the present invention will be described in detail with reference to the accompanying drawings.

Figure 1:
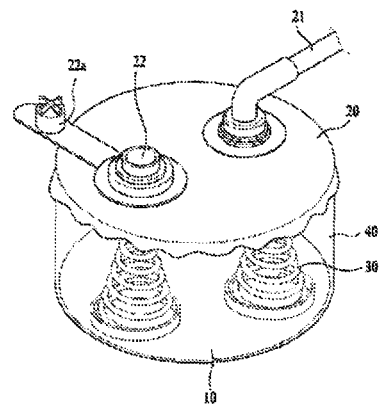
FIG. 1 is a perspective view of an existing medical aspirator.
Figure 2:
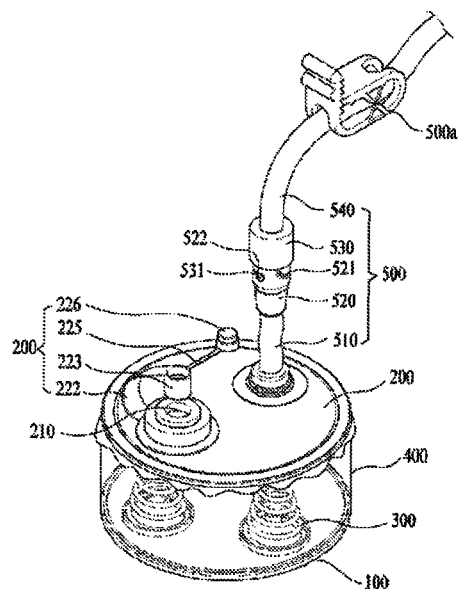
FIG. 2 is a perspective view of a medical aspirator according to the present invention.
Figure 3:
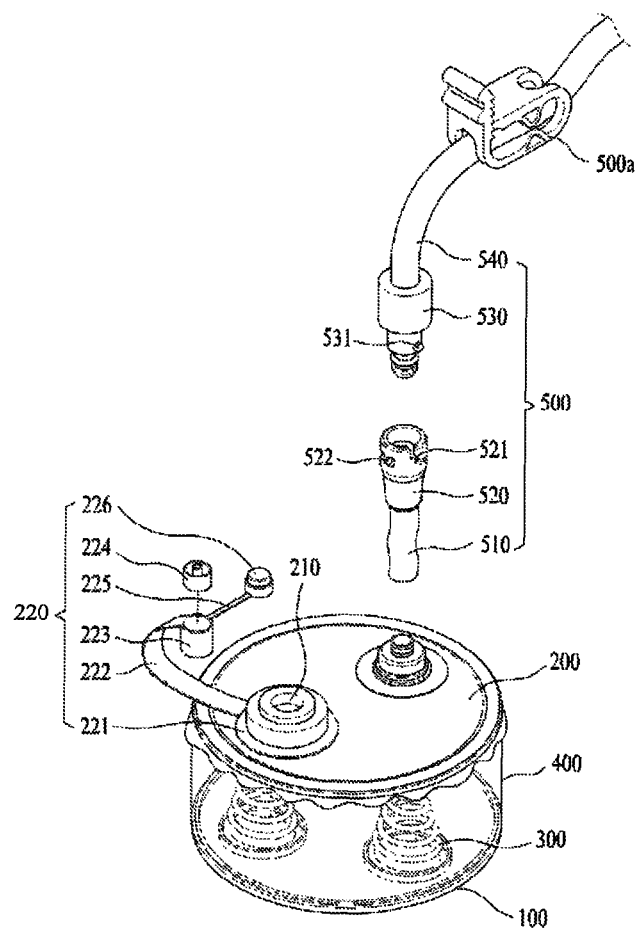
FIG. 3 is an exploded perspective view of the medical aspirator according to the present invention.

FIG. 2 is a perspective view of a medical aspirator according to the present invention. FIG. 3 is an exploded perspective view of the medical aspirator according to the present invention.

Figure 4:
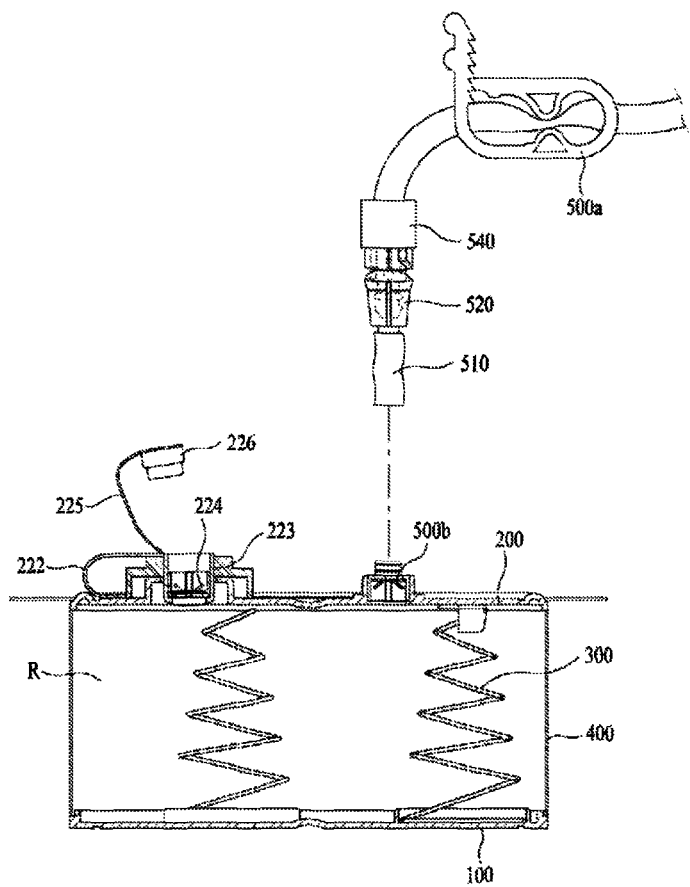
FIG. 4 is a cross-sectional side view of the medical aspirator according to the present invention.
Figure 5:
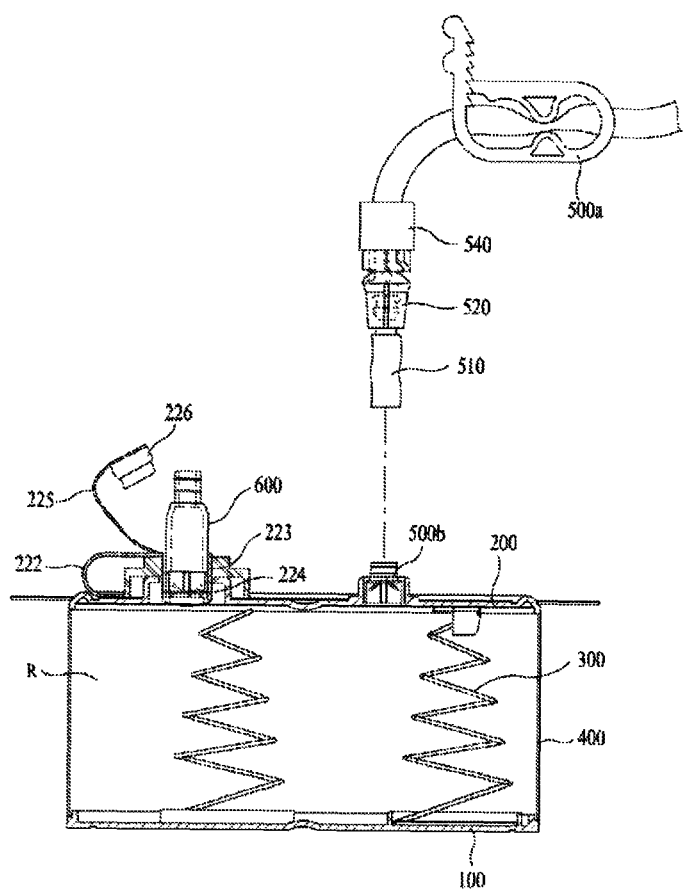
FIG. 5 is a cross-sectional side view showing that a discharge pipe has been connected to the medical aspirator according to the present invention.

FIG. 4 is a side view of the medical aspirator according to the present invention. FIG. 5 is a cross-sectional view showing that a discharge pipe has been connected to the medical aspirator according to the present invention.

The medical aspirator according to the present invention includes a floor plate(100), a pressure plate(200) which is disposed apart from the floor plate(100) by a certain distance, a coil spring(300) which is installed between the floor plate(100) and the pressure plate(200), a sealing membrane (400) which seals between the floor plate(100) and the pressure plate(200), and a drainage tube(500) which is connected to the pressure plate(200).

The floor plate(100) is made of hard synthetic resins in the form of a circular plate.

The pressure plate(200) is disposed upwardly apart from the floor plate(100) by a certain distance and is, like the floor plate(100), made of hard synthetic resins in the form of a circular plate. A discharge hole(210) is formed in the pressure plate(200) and is opened and closed by an opening/closing means(220).

The opening/closing means 220 includes a fixing part 221, a first strap 222 which is integrally connected to the fixing part 221, a fitting tube 223 which is integrally connected to the first strap 222, a check valve 224 which is inserted into the fitting tube 223, a second strap 225 which is integrally connected to the fitting tube 223, and a stopper 226 which is connected to the second strap 225.

The fixing part 221 is fixed around the discharge hole 210 of the pressure plate 200.

The first strap 222 has a thin strip shape and connects the fixing part 221 and the fitting tube 223.

The fitting tube 223 has an inner empty space. The check valve 224 is disposed deep inside the inner surface of the fitting tube 223. The fitting tube 223 is inserted into the discharge hole 210, so that the outer surface of the fitting tube 223 comes in firm contact with the circumferential surface of the discharge hole 210.

The check valve 224 is inserted within the fitting tube 223 and causes fluid to flow only in the direction from the inside of a receiving space "R" formed among the floor plate 100, the pressure plate 200 and the sealing membrane 400 toward the outside of the receiving space "R". Accordingly, after the air within the receiving space "R" is discharged to the outside of the receiving space "R" by pressing the pressure plate 200, even if the force pressing the pressure plate 200 is removed, the external air is not flowed into the receiving space "R".

The second strap 225 is integrally connected to the fitting tube 223 and connects the fitting tube 223 and the stopper 226.

The stopper 226 is integrally connected to the second strap 225 and seals the top of the fitting tube 223 into which the check valve 224 has been inserted. Since when patients or nurses press the pressure plate 200 by mistake after bodily fluids such as blood or exudates generated from the human body are stored in the receiving space "R", the bodily fluids may be leaked to the outside of the receiving space "R". Therefore, the stopper 226 is disposed in order to prevent the leakage of the bodily fluids.

The coil spring 300 has a shape of which a lower end has a larger diameter and an upper end has a smaller diameter. The coil spring 300 provides elasticity to the pressure plate 200 such that the pressure plate 200 is disposed apart from the floor plate 100.

The sealing membrane 400 connects the edge of the floor plate 100 and the edge of the pressure plate 200 and forms the receiving space "R" the bodily fluids between the floor plate 100 and the pressure plate 200. Flow scales is formed in the sealing membrane 400 to check how much bodily fluid has been extracted.

The drainage tube 500 is connected to the pressure plate 200 and guides the bodily fluids generated from the human body to the receiving space "R". A clamp 500a is installed on one side of the drainage tube 500. The clamp 500a controls the flow rate of the bodily fluid which is introduced from the human body. A check valve 500b is disposed between the drainage tube 500 and the pressure plate 200. The check valve 500b causes the fluid to flow only in the direction from the human body to the receiving space "R", and thus, prevents the bodily fluids extracted from the human body from flowing again into the human body.

Describing the drainage tube 500 in more detail, the drainage tube 500 is comprised of a first connecting tube 510, a first connector 520, a second connector 530 and a second connecting tube 540.

The first connecting tube 510 is made of soft synthetic resins such as silicone or PVC and is connected to the pressure plate 200 and communicates with the receiving space "R".

The first connector 520 is fitted to the top of the first connecting tube 510 and is made of hard synthetic resins. A fitting hole 521 passing through the inner and outer surfaces of the first connector 520 is formed in the first connector 520. The fitting hole 521 has a spiral shape or a shape close to a spiral and is formed along the top to the bottom of the first connector 520. Also, a protrusion 522 which slightly protrudes is formed at the end of the fitting hole 521 and reduces the diameter of the fitting hole 521.

The second connector 530 is fitted to the inside of the first connector 520 and is made of hard synthetic resins. An insertion protrusion 531 is formed on the second connector 530. The insertion protrusion 531 moves along the fitting hole 521 formed in the first connector 520. While moving along the fitting hole 521, the insertion protrusion 531 is rotated at the protrusion 522 in an interference fit manner, and then is firmly fixed to the fitting hole 521.

The second connecting tube 540 is fitted to the top of the second connector 530 and is made of soft synthetic resins such as silicone or PVC.

Through the above-described configuration of the drainage tube 500, the drainage tube 500 is easily attachable to and removable from the pressure plate 200. Therefore, when the drainage tube 500 is separated from the pressure plate 200, it is possible to prevent bodily fluids stored in the receiving space "R" from unintentionally getting scattered here and there and to prevent the surrounding from being contaminated or stained by the bodily fluids.

Also, sometimes the bodily fluids stored in the receiving space "R" are required to be discharged due to experiments or for some reasons. In this case, since the bodily fluids can be stably discharged through a drainage tube 600 by connecting the drainage tube 600 to the fitting tube 223, it is possible to prevent the bodily fluids from scattered here and there and to prevent the surrounding from being contaminated or stained by the bodily fluids.

INDUSTRIAL APPLICABILITY

In the medical aspirator according to the present invention, by the check valve, the air within the sealing membrane is flowed out and the external air is not flowed into the sealing membrane, thereby preventing that the bodily fluids stored within the sealing membrane from being contaminated by the external air.

What is claimed is:

1. A medical aspirator comprising:
   a floor plate;
   a pressure plate disposed apart from the floor plate by a certain distance and has a discharge hole being opened and closed by an opening/closing means;
   a coil spring installed between the floor plate and the pressure plate;
   a sealing membrane which connects an edge of the floor plate and an edge of the pressure plate and forms a receiving space configured to receive bodily fluids between the floor plate and the pressure plate; and
   a drainage tube which is connected to the pressure plate and guides the bodily fluids to the receiving space and has a check valve formed therein allowing the fluids generated from a human body to flow only in a direction toward the receiving space from the human body,
   wherein the opening/closing means includes:
      a fixing part which is fixed around the discharge hole of the pressure plate;
      a first strap which is interally connected to the fixing part;
      a fitting tube which is integrally connected to the first strap and is inserted into the discharge hole;
      a check valve which is inserted within the fitting tube such that the fluids are flowed only in a direction toward the outside from the inside of the receiving space;
      a second strap which is integrally connected to the fitting tube; and
      a stopper which is connected to the second strap and seals a top of the fitting tube to which the check valve has been inserted;
   wherein the drainage tube comprises:
   a first connecting tube which is connected to the pressure plate and communicates with the receiving space;
   a first connector which is fitted to a top of the first connecting tube and has a spiral fitting hole formed downwardly therein passing through inner and outer surfaces thereof;
   a second connector which has an insertion protrusion formed on the outer surface thereof in such a manner as to more along the fitting hole of the first connector; and
   a second connecting tube which is fitted to a top of the second connector.

* * * * *